United States Patent [19]

Mizuno et al.

[11] Patent Number: 4,567,282

[45] Date of Patent: Jan. 28, 1986

[54] METHOD OF PRODUCING (S)-GLYCERALDEHYDE ACETONIDE

[75] Inventors: Yukio Mizuno, Ibaraki; Keiichi Sugimoto, Kawanishi, both of Japan

[73] Assignee: Takeda Chemical Industries, Ltd., Osaka, Japan

[21] Appl. No.: 665,435

[22] Filed: Oct. 26, 1984

[30] Foreign Application Priority Data

Oct. 28, 1983 [JP] Japan .................................. 58-203145

[51] Int. Cl.$^4$ ............................................ C07D 317/00
[52] U.S. Cl. .................................................... 549/450
[58] Field of Search ......................................... 549/450

[56] References Cited

PUBLICATIONS

Chem. Abstracts 96:200052n, (1982).
Chem. Abstracts 97:110297n, (1982), (Chemistry Letters), p. 929, (1982).
Journ. Amer. Chem. Soc., pp. 827–828, (Feb., 1952), vol. 74.
Chem. Abstracts 84:17194y, (1976).
Chem. Abstracts 44:3897b, (1950).
Chem. Abstracts 61:5655g, (1964).

*Primary Examiner*—Ethel G. Love
*Attorney, Agent, or Firm*—Wenderoth, Lind & Ponack

[57] ABSTRACT

A method of producing (S)-glyceraldehyde acetonide, which comprises reacting 3,4-O-isopropylidene-L-threonic acid or a salt thereof with hypochlorite ion or hypochlorous acid under an acid condition. Also a method of producing (S)-glyceraldehyde acetonide, which comprises reacting 5,6-O-isopropylidene-L-ascorbic acid or a salt thereof with an oxidizing agent to produce 3,4-O-isopropylidene-L-threonic acid or a salt thereof and then reacting the 3,4-O-isopropylidene-L-threonic acid or a salt thereof with hypochlorite ion or hypochlorous acid under an acid condition. Also a method for producing (S)-glyceraldehyde acetonide, which comprises (1) reacting L-ascorbic acid or a salt thereof with acetone or a conventional equivalent thereof to produce 5,6-O-isopropylidene-L-ascorbic acid or a salt thereof; (2) reacting the 5,6-O-isopropylidene-L-ascorbic acid or a salt thereof with an oxidizing agent to produce 3,4-O-isopropylidene-L-threonic acid or a salt thereof; and (3) reacting the 3,4-O-isopropylidene-L-threonic acid or a salt thereof with hypochlorite ion or hypochlorous acid under an acid condition.

6 Claims, No Drawings

METHOD OF PRODUCING (S)-GLYCERALDEHYDE ACETONIDE

This invention relates to a method of producing (S)-glyceraldehyde acetonide. More particularly, the invention relates to a method of producing (S)-glyceraldehyde acetonide, which comprises reacting 3,4-O-isopropylidene-L-threonic acid or a salt thereof with hypochlorite ion or hypochlorous acid under an acid condition. Also provided is a method of producing (S)-glyceraldehyde acetonide, which comprises reacting 5,6-O-isopropylidene-L-ascorbic acid or a salt thereof with an oxidizing agent to produce 3,4-O-isopropylidene-L-threonic acid or a salt thereof and then reacting the 3,4-O-isopropylidene-L-threonic acid or a salt thereof with hypochlorite ion or hypochlorous acid under an acid condition. Also provided is a method of producing (S)-glyceraldehyde acetonide, which comprises (1) reacting L-ascorbic acid or a salt thereof with acetone or a conventional equivalent thereof to produce 5,6-O-isopropylidene-L-ascorbic acid or a salt thereof; (2) reacting the 5,6-O-isopropylidene-L-ascorbic acid or a salt thereof with an oxidizing agent to produce 3,4-O-isopropylidene-L-threonic acid or a salt thereof; and (3) reacting the 3,4-O-isopropylidene-L-threonic acid or a salt thereof with hypochlorite ion or hypochlorous acid under an acid condition. The reactions involved may be depicted as follows:

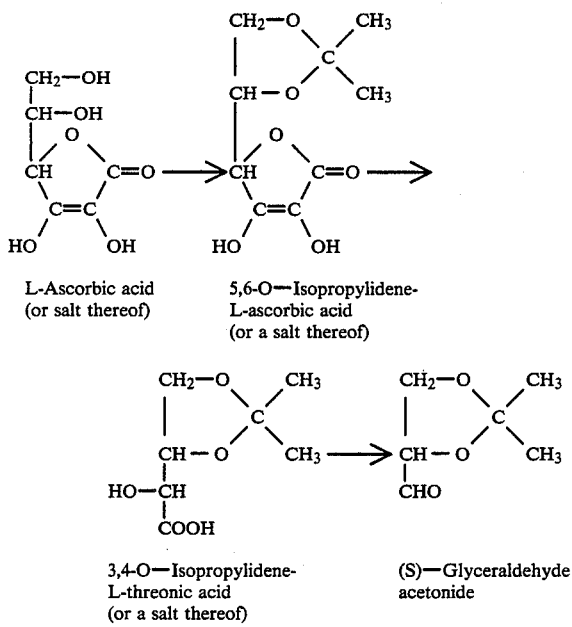

L-Ascorbic acid (or salt thereof)

5,6-O-Isopropylidene-L-ascorbic acid (or a salt thereof)

3,4-O-Isopropylidene-L-threonic acid (or a salt thereof)

(S)-Glyceraldehyde acetonide (S)-Glyceraldehyde acetonide is a compound useful as a starting material for the synthesis of drugs, agricultural chemicals and naturally occurring substances. Several methods of synthesizing (S)-glyceraldehyde acetonide are known. For instance, 5,6-O-isopropylidene-L-ascorbic acid is reduced with sodium borohydride, then hydrolyzed with an alkali, and oxidized with lead tetraacetate [The Journal of the American Chemical Society, 102, 6304 (1980)], or the same starting material, 5,6-O-isopropylidene-L-ascorbic acid, is reduced with lithium aluminum hydride and then oxidized with sodium metaperiodate [Heterocycles, 19, 327 (1982)], or L-gulonic acid γ-lactone, which is obtained by high pressure catalytic reduction of L-ascorbic acid, is protected at positions 5 and 6 by means of acetonide and then oxidized with sodium metaperiodate [Swiss patent application No. 1061/83]. However, the above methods can hardly be used as commercial production methods since they use expensive reagents such as lead tetraacetate, sodium metaperiodate, sodium borohydride and lithium aluminum hydride.

In accordance with the present invention, (S)-glyceraldehyde acetonide is produced by reacting 3,4-O-isopropylidene-L-threonic acid or a salt thereof with hypochlorite ion or hypochlorous acid under an acid condition. The reagents used in this method are all fairly inexpensive. The method according to the invention is also suprior in yield to the prior art methods and therefore suited for its practice on a commercial scale. The starting material 3,4-O-isopropylidene-L-threonic acid or a salt thereof can be produced in an industrially advantageous manner, for instance, by reacting 5,6-O-isopropylidene L-ascorbic acid or a salt thereof with an oxidizing agent. The compound 5,6-O-isopropylidene-L-ascorbic acid or a salt thereof can be produced also in an industrially advantageous manner by reacting L-ascorbic acid or a salt thereof with acetone or a conventional equivalent thereof, for instance.

In practicing the invention, the starting material 3,4-O-isopropylidene-L-threonic acid may be used either in the free acid form or in the form of a conventional salt. As the salt, use is made of alkali metal salt or alkaline earth metal salt, such as sodium salt or calcium salt. The salt may contain water of crystallization (e.g. 1 to 2 moles) and is converted to the free acid in the reaction mixture, so that it can adequately be attacked by hypochlorite ion or hypochlorous acid. The reagent, i.e. hypochlorite ion or hypochlorous acid, can be prepared by conventional methods. Thus, the reagent can be produced, for example, by introducing chlorine gas into water in the presence of mercury or bismuth catalyst, or more conveniently by acidifying an aqueous solution containing a hypochlorite. As such hypochlorite, use is made of an alkali metal salt or alkaline earth metal salt of hypochlorous acid, such as sodium hypochlorite or calcium hypochlorite with a below-mentioned acid. Since the hypochlorite gives hypochlorite ion or hypochlorous acid in an acid condition, the hypochlorite can be used as source of hypochlorite ion or hypochlorous acid. The combination of calcium 3,4-O-isopropylidene-L-threonate dihydrate (hereinafter abbreviated as CIT) as the starting material and a solution of sodium hypochlorite in aqueous sodium hydroxide as the source of hypochlorite ion or hypochlorous acid is more preferable. A strongly alkaline solution of sodium hypochlorite is commercially available, for instance, under the name of Antiformin. In accordance with the invention, 3,4-O-isopropylidene-L-threonic acid or a salt thereof is reacted with hypochlorite ion or hypochlorous acid under acid conditions. The pH value suited for the reaction ranges from about 3 to about 7, preferably from about 4 to about 6. Such conditions may be produced, for example, by adding a mineral acid (e.g. hydrochloric acid, nitric acid) to the reaction system together with the hypochlorite or by adding to the reaction system an acid solution of hypochlorite ion or hypochlorous acid prepared beforehand, with the latter mode being preferred. In the latter case, hypochlorous acid serves in the reaction system both as the acidifying agent and as the mating agent to be reacted with 3,4-O- isopropylidene-L-threonic acid or a salt thereof. Such acid solution of hypochlorite ion or hypochlorous acid may be prepared, for example, by adding an acid such as a mineral acid (e.g. hydrochloric acid, nitric acid) to a hypochlorite or a solution thereof. More particularly, when sodium hypochlorite is used, said hypochlorous acid solution can be prepared by adding hydrochloric acid (concentrated or diluted, preferably 1 to 3N) to the above-mentioned Antiformin cooled, for example, to about 0°–5° C., until the pH becomes preferably about 6. Prior to use, Antiformin can be assayed for available chlorine (5–12 w/v %) by a per se known method, e.g. the method described in The Pharmacopoeia of Japan (10th edition, 1981). It is then used in an amount sufficient to meet the chlorine requirement. Antiformin is generally used in an amount corresponding to about 1–3 equivalents of available chlorine relative to the starting material 3,4-O-isopropylidene-L-threonic acid or a salt thereof.

In the course of the reaction, an appropriate amount of mineral acid (e.g. hydrochloric acid, nitric acid) or a base (e.g. aqueous sodium hydroxide, aqueous sodium carbonate) is added, if desired, in order to maintain the pH within the above acidic range. In carrying out the reaction, the use of a solvent is advantageous to dissolve the starting 3,4-O-isopropylidene-L-threonic acid or a salt thereof. As such solvent, purified water, for instance, is most often used. The solvent is suitably used in an amount at least 5 times (v/w), preferably about 9 times (v/w), relative to the amount of the starting 3,4-O-isopropylidene-L-threonic acid or a salt thereof.

The reaction temperature generally ranges from 0° C. to 70° C. Thus, for instance, the reaction may be started at a temperature of 10° C. or below, followed by gradual temperature elevation to about 35° C. and maintaining this temperature until completion of the reaction. In another embodiment, the reaction may be started at about 50° C., followed by maintaining this temperature throughout the reaction. The latter is also favorable. As for the reaction time, it is advisable to add the reagent hypochlorite ion or hypochlorous acid over 1 to 1.5 hours to the solution containing the starting 3,4-O-isopropylidene-L-threonic acid or a salt thereof and then stir the reaction mixture for further 1 to 1.5 hours until completion of the reaction. However, this condition is not critical. If the progress of the reaction is incomplete due to decomposition of the reagent hypochlorite ion or hypochlorous acid, for instance, an additional amount of the hypochlorite reagent (e.g. hypochlorite, hypochlorite ion, hypochlorous acid) may be added. In accordance with the invention, (S)-glyceraldehyde acetonide can be obtained in high yield (not less than 80%).

If a certain amount of the hypochlorite ion or hypochlorous acid is remaining in the reaction system at the end of the reaction period, sodium thiosulfate may be added in an amount equivalent to the amount of the remaining hypochlorite ion or hypochlorous acid. The reaction mixture as it is (if there is no hypochlorite ion or hypochlorous acid remaining) or after addition of sodium thiosulfate is degasified under reduced pressure and neutralized with a base (e.g. aqueous sodium hydroxide, aqueous sodium carbonate) to give a neutral aqueous solution containing (S)-glyceraldehyde acetonide. The formation of (S)-glyceraldehyde acetonide can be confirmed by adding an organic solvent such as methylene chloride to this aqueous solution, reacting (S)-glyceraldehyde acetonide with a primary amine such as 2,4-dimethoxybenzylamine in the conventional manner and isolating the resulting imine compound (Schiff base). For isolation of (S)-glyceraldehyde acetonide, the above neutral aqueous solution is repeatedly extracted with an organic solvent (e.g. methylene chloride, ethyl acetate) and the extract is dried in the conventional manner. Removal of the solvent by distillation under reduced pressure gives (S)-glyceraldehyde acetonide as a colorless, transparent oil. If necessary, (S)-glyceraldehyde acetonide can be purified by distillation under reduced pressure (boiling point: 64°–66° C./35 mm Hg).

The use of oxidizing agents other than the hypochlorite (e.g. hypochlorite, hypochlorite ion, hypochlorous acid), which is used in accordance with the present invention, in the oxidation of CIT either failed to give (S)-glyceraldehyde acetonide but gave glyceric acid acetonide (when potassium permanganate was used), or gave only a poor yield (20–30%) of (S)-glyceraldehyde acetonide (when aqueous hydrogen peroxide was used in the presence of ferric acetate).

3,4-O-Isopropylidene-L-threonic acid or a salt thereof can be synthesized in the following manner. Thus, 5,6-O-isopropylidene-L-ascorbic acid or a salt thereof (e.g. alkali metal salt or alkaline earth metal salt, such as sodium salt or calcium salt) is reacted with an oxidizing agent to produce 3,4-O-isopropylidene-L-threonic acid or a salt thereof. As such oxidizing agent, use may be made of hydrogen peroxide, sodium permanganate, potassium permanganate, etc. Among others, hydrogen peroxide (preferably aqueous hydrogen peroxide) is advantageously used. The oxidizing agent is usually used in an amount of 1 to 10 moles (preferably 1 to 5 moles) relative to the starting 5,6-O-isopropylidene-L-ascorbic acid. The above oxidation reaction is generally carried out by a per se known method, usually in a solvent. As the solvent, use is made of conventional solvents which do not adversely affect the reaction, such as water, etc. The solvent used is suitably selected depending upon the oxidizing agent according to existing knowledge. The reaction temperature is not particularly critical and generally ranges from $-5°$ C. to $70°$ C. The reaction is conveniently carried out at room temperature (e.g. 10° C.–30° C.) or under warming (e.g. 30° C.–70° C.). The reaction time is not critical and the reaction usually goes to completion in 10 minutes to 5 hours. Such conditions are chosen according to the known technique in the art of oxidation. The resulting 3,4-O-isopropylidene-L-threonic acid or a salt thereof can be isolated and purified by a per se known method such as concentration, change of pH, change of solvent, solvent extraction and chromatography. 3,4-O-Isopropylidene-L-threonic acid may be obtained either in the form of acid or in the form of its salt (e.g. alkali metal salt or alkaline earth metal salt, such as sodium salt or calcium salt). Most conveniently, 3,4-O-isopropylidene-L-threonic acid can be obtained as a calcium salt dihydrate (CIT) in the form of white crystals, but the reaction mixture, as such without being isolated, may be used as a starting material in the subsequent step. [U.S. patent application No. 448,116, filed Dec. 9, 1982, now U.S. Pat. No. 4,502,994].

5,6-O-Isopropylidene-L-ascorbic acid or a salt thereof can be synthesized, for example, in the following manner. Thus, L-ascorbic acid or a salt thereof (e.g. alkali metal salt or alkaline earth metal salt, such as sodium salt or calcium salt) is reacted, for example, with acetone or a conventional equivalent thereof, preferably in the presence of an acid catalyst such as a mineral acid (e.g. hydrogen chloride, sulfuric acid, nitric acid) or an organic acid (e.g. p-toluenesulfonic acid, etc.). As the conventional equivalent to acetone, use is made of 2,2-di-($C_{1-4}$ alkoxy)propane or 2-($C_{1-4}$ alkoxy)propene. As such $C_{1-4}$ alkoxy, use is made of methoxy, ethoxy, n-propoxy, n-butoxy, etc. Frequent use is made of 2,2-dimethoxypropane, 2,2-diethoxypropane or 2-methoxypropene as the conventional equivalent of acetone. Acetone or a conventional equivalent thereof is usually used in an amount of 1 to 20 moles (preferably 1 to 5 moles) relative to L-ascorbic acid or a salt thereof. The reaction is usually carried out in a solvent. As the solvent, use is made of conventional solvents such as acetone, N,N-dimethylformamide, methanol, ethanol, etc. Acetone can also function as a solvent. In case acetone is used both as a reagent and as a solvent, a large excess amount of acetone can be used. The reaction temperature is not particularly restricted and the reaction is conveniently carried out at room temperature (e.g. 10° C.–30° C.) or under warming (e.g. 30° C.–100° C.), and goes to completion in a few minutes (e.g. 1 min.–30 min.) to several days (e.g. 1 day–5 days). The resulting 5,6-O-isopropylidene-L-ascorbic acid can be isolated and purified by a per se known method such as concentration, crystallization and recrystallization. 5,6-O-Isopropylidene-L-ascorbic acid may be obtained either in the form of acid or in the form of its salt (e.g. alkali metal or alkaline earth metal salt, such as sodium salt or calcium salt). However, the reaction mixture, as such without being isolated, may be used as a starting material in the subsequent step. [U.S. patent application No. 448,116].

As described above, the present invention has a characteristic of producing (S)-glyceraldehyde acetonide through subjecting 5,6-O-isopropylidene-L-ascorbic acid to a series of oxidation reactions, while prior art methods consist of combination of reduction and oxidation starting from L-ascorbic acid or 5,6-O-isopropylidene-L-ascorbic acid.

(S)-Glyceraldehyde acetonide produced in accordance with the invention is a compound useful as a starting material for the synthesis of various drugs, agricultural chemicals, naturally occurring substances, etc. For instance, it is used in the synthesis of an antiepileptic, antihypertensive agent GABOB [(R)-(−)-γ-amino-β-hydroxybutyric acid]. [The Journal of the Americal Chemical Society, 102, 6304 (1980)]. The imine compound (Schiff base) resulting from the reaction between (S)-glyceraldehyde acetonide and a primary amine undergoes stereoselective ring closure upon reaction with a variety of acid chlorides or active esters in the presence of a base under formation of the β-lactam ring. More specifically, the reaction of (S)-glyceraldehyde acetonide 2,4-dimethoxybenzylimine and N-phthaloylglycine chloride in the presence of triethylamine gives N-[(3S,4S)-cis-1-(2,4-dimethoxybenzyl)-4-[(R)-2,2-dimethyl-1,3-dioxolan-4-yl]-2-oxo-3-azetidinyl]phthalimide in high yield and high stereospecificity. [Swiss patent application No. 3416/82]. The latter compound is especially useful as an intermediate for the synthesis of various single β-lactam antibiotics such as a novel, broad-spectrum monobactam antibiotic (3S,4S)-3-[2-(2-amino-4-thiazolyl)-(Z)-2-(carboxymethoxyimino)acetamido]-4-carbamoyloxymethyl-2-azetidinone-1-sulfonic acid (AMA-1080) [Swiss patent application Nos. 5524/81, 3416/82 and 3417/82].

The present invention is further illustrated in greater detail by the following examples, but they are not to be construed as limiting the present invention.

EXAMPLE 1

In 20 ml of pure water was dissolved 2.31 g of CIT, and the solution was cooled to 5° C. and adjusted to pH 5 with 2N hydrochloric acid. To this solution were simultaneously added dropwise 7.5 ml of Antiformin (available chlorine: 10 w/v %) and 7 ml of 2N hydrochloric acid while maintaining the reaction mixture at pH 4.5 to 5.5 and the resultant mixture was stirred at 10° C. or below for 30 minutes. Then, the temperature was raised to 25° C. over a period of 30 minutes, followed by stirring at the same temperature for an hour. Further, to the reaction mixture were simultaneously added dropwise 1.0 ml of the above Antiformin and 2N hydrochloric acid at the same temperature and the resultant mixture was stirred at the same temperature for an hour while maintaining the pH at 4.5 to 5.5. To the mixture was added 0.2 g of sodium thiosulfate to terminate the reaction. The reaction mixture was degasified under reduced pressure, adjusted to pH 7 with aqueous sodium hydroxide, saturated with sodium chloride and extracted with five 30-ml portions of methylene chloride and four 30-ml portions of ethyl acetate. The extracts were combined and dried over anhydrous magnesium sulfate. The solvent was then distilled off under reduced pressure to give 1.0 g of oil. This oil was distilled under reduced pressure in a micro distillation apparatus to give 780 mg (60% yield) of (S)-glyceraldehyde acetonide. B.p. 64°–66° C./35 mm Hg.

$^1$H NMR spectrum (CDCl$_3$): δ9.77(1H, broad, s), δ1.49(3H, s), δ1.42(3H, s).

EXAMPLE 2

In 800 ml of pure water was dissolved 92.4 g of CIT and the solution was cooled to 5° C. and adjusted to pH 6 with 1N hydrochloric acid. Separately, 230 ml of Antiformin (available chlorine: 10 w/v %) was cooled to 5° C. and adjusted to pH 6 by dropwise addition of 3N hydrochloric acid. This weakly acidic solution was added to the above CIT solution and the mixture was stirred at 10° C. or below for 30 minutes while maintaining the pH at 5 to 6. Then, the temperature was raised to 30° C. over a period of 30 minutes, followed by stirring at the same temperature for 30 minutes. The reaction mixture was cooled again to 5° C. and the weakly acidic Antiformin solution prepared from 115 ml of Antiformin in the above manner was added, followed by stirring at 10° C. or below for 30 minutes. Then, the temperature was raised to 35° C. over a period of 30 minutes and the mixture was stirred at the same temperature for an hour. During the reaction period, 1N hydrochloric acid or 1N sodium hydroxide was added dropwise if desired to maintain the pH at 5 to 6. Thereafter, 1.0 g of sodium thiosulfate was added to stop the reaction, and the reaction mixture was degasified under reduced pressure and adjusted to pH 7 with aqueous sodium hydroxide.

To the neutralized reaction mixture was added 1 liter of methylene chloride, and 53.6 g of 2,4-dimethoxybenzylamine was added in a nitrogen gas stream at 10° C. or below. The mixture was vigorously stirred for 30 minutes. Then, the temperature was raised to 25° C. over a period of 30 minutes, followed by stirring at the same temperature for an hour. The aqueous layer was separated and reextracted with 500 ml of methylene chloride. The extracts were combined and washed with three 200-ml portions of saturated aqueous ammonium chloride and 200 ml of water and dried over anhydrous magnesium sulfate. The methylene chloride was then distilled off under reduced pressure to give 82.0 g (73% yield) of (S)-glyceraldehyde acetonide 2,4-dimethoxybenzylimine.

$^1$H NMR spectrum (CDCl$_3$): δ7.66(1H, m).

EXAMPLE 3

In 80 ml of pure water was dissolved 9.24 g of CIT and the solution was warmed to 50° C. and adjusted to pH 5 with 1N hydrochloric acid. To this solution was added dropwise an aqueous solution with pH 6 prepared from 44 ml of Antiformin (available chlorine: 6.3 w/v %) over a period of 30 minutes, followed by dropwise addition of an aqueous solution with pH 6 prepared from 22 ml of the above Antiformin over a period of 30 minutes. After completion of the addition, the mixture was stirred at the same temperature for 45 minutes, during which time, 1N hydrochloric acid or 1N sodium hydroxide was added if desired to maintain the pH at 5. The reaction mixture was cooled to 25° C., degasified under reduced pressure and adjusted to pH 7 with 1N sodium hydroxide. To the neutralized reaction mixture was added 100 ml of methylene chloride, and 6.0 g of 2,4-dimethoxybenzylamine was then added in a nitrogen gas stream at 10° C. The mixture was vigorously stirred for 30 minutes. Then, the temperature was raised to 25° C. over a period of 30 minutes, followed by stirring at the same temperature for an hour. The aqueous layer was separated and reextracted with 50 ml of methylene chloride. The extracts were combined, washed with two 90-ml portions of saturated aqueous boric acid and 90 ml of pure water and dried over anhydrous magnesium sulfate. The methylene chloride was distilled off under reduced pressure to give 8.03 g (72% yield) of (S)-glyceraldehyde acetonide 2,4-dimethoxybenzylimine.

EXAMPLE 4

In 80 ml of pure water was dissolved 9.24 g of CIT at 30° C., and 2.12 g of sodium carbonate was added. The mixture was stirred for an hour. The insoluble substance was removed with the aid of Hyflo Super-Cel (Johns-Manville Sales Corp.) and the aqueous solution was concentrated to dryness. To the residue was added 60 ml of pure water for dissolution and the solution was adjusted to pH 5 by addition of 1N hydrochloric acid at 25° C. To this solution was added dropwise a solution of pH 6 prepared from 35.8 ml of Antiformin (available chlorine 7.9 w/v %) over a period of 30 minutes followed by dropwise addition of a solution of pH 6 prepared from 17 ml of Antiformin over a period of 30 minutes. After completion of the addition, the temperature was raised to 35° C. over a period of 10 minutes, followed by stirring at the same temperature for 45 minutes. During the reaction period, 1N hydrochloric acid or 1N sodium hydroxide was added dropwise if desired to maintain the pH at 5.3 to 5.5. To the reaction mixture was added 0.2 g of sodium thiosulfate to treat the excess hypochlorite ion therewith and the mixture was degasified under reduced pressure for 10 minutes and neutralized to pH 7 with 1N sodium hydroxide.

To the above reaction mixture was added 100 ml of methylene chloride, and 6.0 g of 2,4-dimethoxybenzylamine was added in a nitrogen gas stream at 10° C. The mixture was vigorously stirred for 30 minutes. Then, the temperature was raised to 25° C. over a period of 30 minutes, followed by vigorous stirring at the same temperature for an hour. The aqueous layer was separated and reextracted with 50 ml of methylene chloride. The extracts were combined and washed with two 90-ml portions of saturated aqueous boric acid and 90 ml of pure water and dried over anhydrous magnesium sulfate. The methylene chloride was distilled off under reduced pressure to give 6.94 g (62% yield) of (S)-glyceraldehyde acetonide 2,4-dimethoxybenzylimine as an oil.

EXAMPLE 5

In 400 ml of pure water was suspended 43.2 g of 5,6-O-isopropylidene-L-ascorbic acid, and 40 g of calcium carbonate was added. The mixture was cooled and 80 ml of 30% aqueous hydrogen peroxide was added dropwise while maintaining the temperature at 10° C. or below. Thereafter, the temperature was raised to 20° C. over a period of an hour, followed by stirring at the same temperature for 2 hours and at 30° to 35° C. for 30 minutes. To the reaction mixture were portionwise added 8 g of activated carbon and 1 g of 10 w/w % palladium-on-carbon (50 w/w % hydrous) to treat the unreacted hydrogen peroxide therewith and the mixture was cooled, followed by removal of the insoluble substance with the aid of Hyflo Super-Cel to give 650 ml of an aqueous solution containing CIT. Thereafter, according to the procedure of Example 2 there was synthesized (S)-glyceraldehyde acetonide and the acetonide was then converted to (S)-glyceraldehyde acetonide 2,4-dimethoxybenzylimine. The yield of the imine was 39.3 g (70% overall yield from 5,6-O-isopropylidene-L-ascorbic acid).

EXAMPLE 6

The mixture of 80 ml of acetone, 16 g of L-ascorbic acid and 18.8 ml of 2,2-dimethoxypropane was stirred for 15 minutes at room temperature. Hydrogen chloride was added slowly through bubbler to the reaction mixture over 5 minutes and the mixture was stirred for 1 hr at room temperature. Half volume of acetone was evaporated off under reduced pressure. The mixture was cooled in an ice bath, and the resulting precipitates were filtered and washed with 30 ml of cold acetone to give 15.2 g of 5,6-O-isopropylidene-L-ascorbic acid. Then mother liquor was concentrated to give 3.8 g of 5,6-O-isopropylidene-L-ascorbic acid.

The obtained acetonides were combined and suspended in 180 ml of pure water and 17.6 g of calcium carbonate was added thereto. The mixture was cooled and 35.2 ml of 30% aqueous hydrogen peroxide was added dropwise while maintaining the temperature at 10° C. or below. Thereafter, the temperature was raised to 20° C. over a period of an hour, followed by stirring at the same temperature for 2 hours and at 30° to 35° C. for 30 minutes. To the reaction mixture were portionwise added 4 g of activated carbon and 0.5 g of 10 w/w % palladium-on-carbon (50 w/w % hydrous) to treat the unreacted hydrogen peroxide therewith and the mixture was cooled, followed by removal of the insoluble substance with the aid of Hyflo Super-Cel to give 280 ml of an aqueous solution containing CIT.

The resulting aqueous solution of CIT was warmed to 50° C. and adjusted to pH 5 with 1N hydrochloric acid. To this solution was added dropwise an aqueous solution with pH 6 prepared from 90 ml of Antiformin (available chlorine: 6.3 w/v %) over a period of 30 minutes, followed dropwise addition of an aqueous solution with pH 6 prepared from 45 ml of the above Antiformin over a period of 30 minutes. After completion of the addition, the mixture was stirred at the same temperature for 45 minutes, during which time, 1N hydrochloric acid or 1N sodium hydroxide was added if desired to maintain the pH at 5. The reaction mixture was cooled to 25° C., degasified under reduced pressure and adjusted to pH 7 with 1N sodium hydroxide. To the neutralized reaction mixture was added 200 ml of methylene chloride, and 12.5 g of 2,4-dimethoxybenzylamine was then added in a nitrogen gas stream at 10° C. The mixture was vigorously stirred for 30 minutes. Then, the temperature was raised to 25° C. over a period of 30 minutes, followed by stirring at the same temperature for an hour. The aqueous layer was separated and reextracted with 100 ml of methylene chloride. The extracts were combined, washed with two 200-ml portions of saturated aqueous boric acid and 200 ml of pure water and dried over anhydrous magnesium sulfate. The methylene chloride was distilled off under reduced pressure to give 17.2 g (68% yield from L-ascorbic acid) of (S)-glyceraldehyde acetonide 2,4-dimethoxybenzylimine.

EXAMPLE 7

In 300 ml of pure water was dissolved 34.7 g of CIT at 50° C. and the solution was adjusted to pH 5 with 3N hydrochloric acid. To this solution were simultaneously added dropwise at 50° C. 83.4 g of Antiformin (available chlorine: 13.4 w/w %) and 46.5 ml of 3N hydrochloric acid over a period of 30 minutes while maintaining the reaction mixture at pH 4.8 to 5.2. The resultant mixture was stirred at the same temperature for further 20 minutes while adding if desired 1N sodium hydroxide to maintain the pH at 4.8 to 5.2. After completion of the reaction, work-up as mentioned in above examples gave an aqueous solution containing 15.6 g (80% yield) of (S)-glyceraldehyde acetonide.

The yield of (S)-glyceraldehyde acetonide was determined by gas-chromatographic method using anisole as an internal standard.

Reference Example 1

In 500 ml of methylene chloride was dissolved 80 g of the imine compound (Schiff base) as obtained in Examples 2 to 5, and the solution was cooled to 0° C., followed by addition of 56 ml of triethylamine. And then, a solution of 66.4 g of N-phthaloylglycine chloride in 90 ml of methylene chloride was added dropwise at 0° C., and the mixture was stirred at 25° C. for 2 hours. After pure water was added, the methylene chloride layer was separated and washed with three 300-ml portions of pure water, 100 ml of 1N hydrochloric acid, two 150-ml portions of saturated aqueous sodium hydrogen carbonate, two 150-ml portions of pure water and 150 ml of saturated aqueous sodium chloride in that order and dried over anhydrous magnesium sulfate. The solvent was then distilled off under reduced pressure to give 125 g of a solid. This product, when assayed by liquid chromatography, had a purity of about 85% (by area percentage calculation). This product was dissolved in 100 ml of ethyl acetate, cooled to −20° C. and allowed to stand overnight to give 66.0 g (50% yield) of N-[(3S,4S)-cis-1-(2,4-dimethoxybenzyl)-4-[(R)-2,2-dimethyl-1,3-dioxolan-4-yl]-2-oxo-3-azetidinyl]phthalimide. M.p. 155° C. $[\alpha]_D^{20} = +48°$ (c=0.6, CHCl$_3$).

What we claim is:

1. A method of producing (S)-glyceraldehyde acetonide, which comprises reacting 3,4-O-isopropylidene-L-threonic acid or a salt thereof with hypochlorite ion or hypochlorous acid under an acid condition.

2. A method of producing (S)-glyceraldehyde acetonide, which comprises reacting 5,6-O-isopropylidene-L-ascorbic acid or a salt thereof with an oxidizing agent to produce 3,4-O-isopropylidene-L-threonic acid or a salt thereof and then reacting the 3,4-O-isopropylidene-L-threonic acid or a salt thereof with hypochlorite ion or hypochlorous acid under an acid condition.

3. A method of producing (S)-glyceraldehyde acetonide, which comprises (1) reacting L-ascorbic acid or a salt thereof with acetone or a conventional equivalent thereof to produce 5,6-O-isopropylidene-L-ascorbic acid or a salt thereof, (2) reacting the 5,6-O-isopropylidene-L-ascorbic acid or a salt thereof with an oxidizing agent to produce 3,4-O-isopropylidene-L-threonic acid or a salt thereof, and (3) reacting the 3,4-O-isopropylidene-L-threonic acid or a salt thereof with hypochlorite ion or hypochlorous acid under an acid condition.

4. A method according to claim 1, wherein the reaction of 3,4-O-isopropylidene-L-threonic acid or a salt thereof with hypochlorite ion or hypochlorous acid is carried out at the pH value from about 3 to about 7.

5. A method according to claim 2, wherein the reaction of 3,4-O-isopropylidene-L-threonic acid or a salt thereof with hypochlorite ion or hypochlorous acid is carried out at the pH value from about 3 to about 7.

6. A method according to claim 3, wherein the reaction of 3,4-O-isopropylidene-L-threonic acid or a salt thereof with hypochlorite ion or hypochlorous acid is carried out at the pH value from about 3 to about 7.

* * * * *